United States Patent [19]

Okimoto

[11] Patent Number: 4,945,921
[45] Date of Patent: Aug. 7, 1990

[54] BODY CAVITY SPECIMEN COLLECTING AND TESTING APPARATUS

[76] Inventor: Paul M. Okimoto, 638 Cornell, Albany, Calif. 94706

[21] Appl. No.: 139,621

[22] Filed: Dec. 30, 1987

Related U.S. Application Data

[63] Continuation-in-part of Ser. No. 87,807, Aug. 21, 1987, Pat. No. 4,784,158.

[51] Int. Cl.⁵ .............................................. A61B 10/00
[52] U.S. Cl. ...................................... 128/759; 128/771
[58] Field of Search ............................... 128/749–759; 206/569

[56] References Cited

U.S. PATENT DOCUMENTS

| | | |
|---|---|---|
| 2,664,879 | 1/1954 | Hardy . |
| 2,945,491 | 7/1960 | Gibbs . |
| 3,017,879 | 1/1962 | Sapit et al. . |
| 3,037,495 | 6/1962 | Naz ...................... 128/759 |
| 3,037,496 | 6/1962 | Melges . |
| 3,117,569 | 1/1964 | Wegner . |
| 3,272,319 | 9/1966 | Brewer . |
| 3,507,269 | 4/1970 | Berry . |
| 3,552,929 | 1/1971 | Fields et al. . |
| 3,572,997 | 3/1971 | Burk . |
| 3,800,781 | 4/1974 | Zalucki ................. 128/749 |
| 3,990,850 | 11/1976 | Friedman et al. . |
| 4,023,559 | 5/1977 | Gaskell ................. 128/759 |
| 4,157,709 | 6/1979 | Schuster et al. ....... 128/759 |
| 4,628,941 | 12/1986 | Kosasky ................ 128/759 |

*Primary Examiner*—Max Hindenburg
*Attorney, Agent, or Firm*—Flehr, Hohbach, Test, Albritton & Herbert

[57] ABSTRACT

A self-testing apparatus (21) and method for collecting and testing a specimen from a body cavity, and particularly the vagina. The apparatus (21) includes a collecting instrument (22, 61, 81) formed with a hollow body (27, 62, 88) and a reciprocally mounted plunger (31, 63, 82) inside the body (27, 62, 88) that is spring biased to a rectracted position inside the body. Mounted on the end of the plunger (31, 63, 82) is a material (44, 67, 84) capable of absorbing bodily fluids. The self-testing kit (21) further includes an independent testing assembly (23) which is used after the collecting assembly (22, 61, 81) collects the specimen. The collected specimen can be wiped across a treated paper (51) with the reaction compared to a color chart (52) mounted proximate the treated paper (51).

6 Claims, 4 Drawing Sheets

BODY CAVITY SPECIMEN COLLECTING AND TESTING APPARATUS

RELATED APPLICATION

The present application is a continuation-in-part application based upon co-pending application Ser. No. 87,807 filed Aug. 21, 1987, for VAGINAL TESTING APPLICATOR AND METHOD, now U.S. Pat. No. 4,784,158.

TECHNICAL FIELD

The present invention relates, in general, to an apparatus and method for collecting and testing a fluid specimen taken from a body cavity to determine the condition of such fluid, and more particularly, the invention relates to a self-testing apparatus and method for determining the acidity level of the human vagina.

BACKGROUND ART

Typically, the vagina of a healthy human female has a pH of less than 4.5. It is well known that an elevated pH occurs among women with a variety of bacterial infections. Determining the pH level of the vagina is usually done by a doctor or clinician in a doctor's office because false readings are easily obtained if the procedure is not carried out properly, e.g., if the pH paper used comes in contact with outer vaginal secretions, cervical secretions or urine. Such contact can yield false pH readings in the high range, possibly provoking an unnecessary visit to a doctor's office, or in the low range, urine contamination which could yield a false negative response and a delay in treatment with potentially serious consequences.

There are few, if any, self-testing devices presently in use as a result of this contamination problem. Accordingly, it would be advantageous to provide a reusable vaginal testing applicator assembly which would minimize the hazard of obtaining false readings through contact with contaminating substances.

The patent literature includes body cavity testing apparatus in which a treated or test paper, such as pH paper, has been employed to determine fertility and/or ovulation. Thus, U.S. Pat. Nos. 2,945,491, 3,017,897, 3,037,496 and 3,117,569 are all examples of applicator or test apparatus which has been used to test for fertility or ovulation. In each of these patents, an instrument is provided for insertion of the test paper into the body cavity, in this case, the vagina, so that the paper can be contacted with bodily fluids to conduct a test of the condition of the fluids in the vagina.

In U.S. Pat. Nos. 2,945,491 and 3,117,569, the testing paper is affixed to the end of the applicator or instrument body and is not capable of being shielded during insertion or removal from the vagina. In U.S. Pat. Nos. 3,017,879 and 3,037,496, the treated papers or testing members can be retracted into the housing of the applicator bodies so as to shield the same during insertion and removal from the vagina. Thus, the test paper tends not to become contaminated by vaginal secretions or urine during the insertion and removal processes.

One problem which has been encountered in connection with such vaginal secretion testing apparatus is that the test paper or treated test material can become overwhelmed by the bodily fluids. This is particularly true when bacterial infections are present. The test paper or material, therefore, can loose its mechanical integrity and/or yield false readings as a result of the excess fluids. Moreover, while trained physicians can develop and perfect their testing techniques was to try to minimize the possibility of contamination, unskilled users when attempting self-testing may not fully retract the test paper during insertion and removal.

U.S. Pat. No. 2,664,879 discloses a similar body testing apparatus in which pH paper can be inserted into a body cavity, such as the vagina, and the test paper compared to a color chart once a specimen has been contacted with the paper. Again, the primary problem with such apparatus is that there is no shielding of the test paper, and the paper can be easily overwhelmed by bodily fluids.

The use of comparison charts or test strips in connection with medical diagnostic apparatus is broadly known in the prior art. Thus, U.S. Pat. Nos. 3,272,319, 3,507,269, 3,552,929, 3,572,997 and 3,990,850 are all examples of biological testing apparatus in which the effect of a test specimen on a test material is compared to a known chart or strip. Such comparison allows a match between the unknown test sample and the known chart colors to enable a diagnosis to be made.

Accordingly, it is an object of the present invention to provide a body cavity specimen collecting and testing apparatus and method which can be easily used by untrained personnel for self-testing of the condition of fluids in a body cavity.

Another object of the present invention is to provide a body cavity specimen collecting and testing apparatus and method which has improved reliability and will not be overwhelmed by an excess of bodily fluids.

Still further an object of the present invention is to provide a vaginal specimen collecting and testing apparatus which is simple and inexpensive to construct and is easy to use.

The body cavity specimen collecting and testing apparatus of the present invention has other objects and features of advantage which will become apparent from or are set forth in more detail in the following description of the best mode of carrying out the invention and the accompanying drawing.

DISCLOSURE OF THE INVENTION

The body cavity specimen collecting and testing apparatus of the present invention includes an elongated hollow body dimensioned for insertion into a body cavity, which hollow body has an open front end and an open opposite end. Mounted for reciprocation in the hollow body is a plunger with a first end proximate the open front end of the body and a manually engageable second end extending outwardly of the opposite end of the body. A specimen contacting member is carried by the first end of the plunger and is dimensioned to pass through the open front end of the body, and the plunger is mounted for reciprocation between an extended position with the specimen contacting member extending beyond the open front end and a retracted position with the specimen contacting member retracted inside the hollow body.

The improvement in the specimen collecting and testing apparatus of the present invention comprises, briefly, the specimen contacting member being formed of a material suitable for collecting a sufficient quantity of bodily fluids from the body cavity to enable transfer of a specimen of such fluids to a separate specimen testing assembly after contact of the specimen contact member with the body fluids and removal of the testing apparatus from the body cavity; and a biasing member resiliently biasing the plunger to a retracted position to automatically shield the specimen contacting member from contamination by bodily fluids during insertion and removal of the apparatus upon release of the manual engageable end of the plunger.

In one embodiment of the invention a resilient sponge material is employed as both the specimen contacting and collecting member and the spring biasing member. In another embodiment, a continuous elastic band is used as a spring biasing member and an absorbent cotton material is used as the specimen contacting member. Finally, a concentrically mounted coil spring is employed as the biasing member around an absorbent cotton collecting member.

The body cavity specimen collecting and testing apparatus of the present invention further includes a specimen testing assembly in which there is a strip of treated test paper or material mounted proximate a color chart. After collecting the specimen, the specimen contacting member can be extended from the hollow body and wiped across the testing strip to contact the testing strip with the fluids to be tested. Thereafter, the testing strip and the color chart can be compared to diagnose the condition of the body cavity.

The method of testing the condition of a fluid in a body cavity of the present invention comprises, briefly, the steps of inserting a shielded fluid absorbing member into the body cavity, contacting the absorbing member with fluids in the cavity, withdrawing the member while shielded, and after withdrawal, contacting the absorbing member with a treated test strip.

BEST MODE OF CARRYING OUT THE INVENTION

Apparatus for the testing of the condition of bodily fluids have previously been based upon simply contacting the test material, such as pH paper, with the fluid to be tested. The apparatus of the present invention is used, by contrast, by first collecting a specimen of the bodily fluid in a manner which shields the specimen from contamination and thereafter and outside the body, contacting the fluid specimen with a test material or paper to effect testing.

Figures 1, 2:
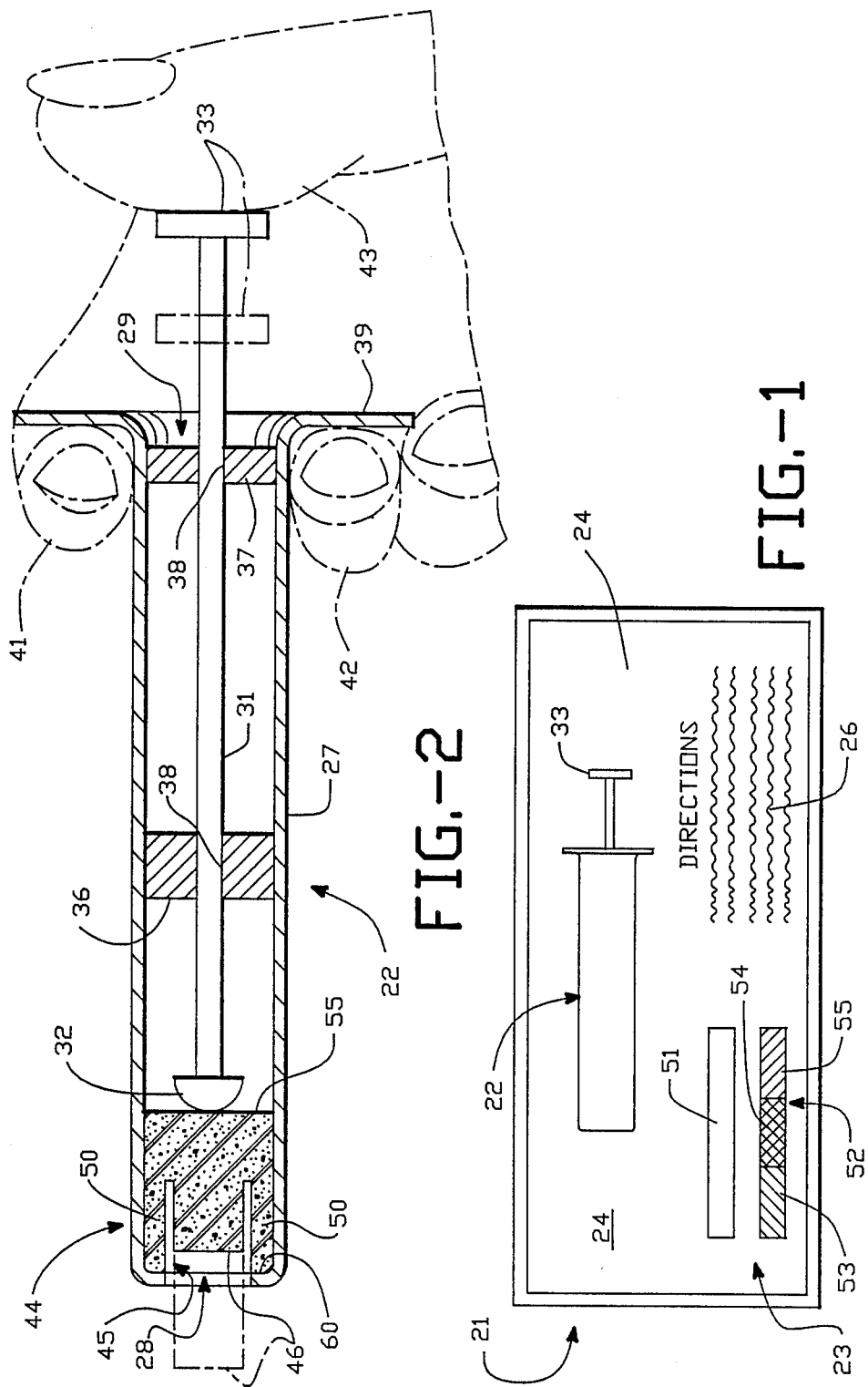
FIG. 1 is a top plan view of a body cavity specimen collecting and testing kit constructed in accordance with the present invention.
FIG. 2 is an enlarged, side elevation view, in cross section, of a specimen collecting apparatus from the kit of FIG. 1.

Referring to FIG. 1, a kit, generally designated 21, is shown in which there is a specimen collecting apparatus, generally designated 22, and a specimen testing means, generally designated 23. Collecting apparatus 22 is removably mounted to a cardboard or plastic mounting base 24, which also carries the testing assembly 23 and which also has a set of directions 26 as to the use of the kit printed on card 24.

In order to prevent contamination of kit 21, card 24 is further preferably enclosed by a water impervious envelope (not shown). Specimen testing apparatus 23 is preferably fixedly secured to card 24, while specimen collecting apparatus 22 can be removably secured to card 24 by a pressure sensitive adhesive or, for example, by vacuum sealing the water impervious envelope to the card. As will also be understood, the specimen collecting apparatus and specimen testing means or assembly 23 can be provided as separate assemblies which are separately packaged or placed in the same package, as a matter of choice and convenience.

In order to prevent overwhelming of the test materials, the apparatus of the present invention preferably includes a specimen collecting apparatus instead of an apparatus to insert or apply the test paper to the fluids in the body cavity. The collecting apparatus of FIG. 2, for example, includes an elongated hollow body 27 having a diameter dimensioned for insertion into a canal or track leading to or comprising a body cavity. Most preferably, the diameter of hollow body 27 is dimensioned for insertion into the vagina of a human. Body 27 has an open front end 28 and an open opposite end 29. Mounted for reciprocation inside the hollow body 27 is plunger means 31 which has a first end 32 positioned proximate open end 28 of the hollow collector body and a second manually engageable end 33 extending outwardly of opposite end 29 of the hollow body. Guided reciprocation of plunger means 31 is advantageously accomplished by providing guide means or blocks 36 and 37 fixedly mounted inside the hollow body. Each of blocks 36 and 37 has a central bore 38 dimensioned for sliding receipt of plunger 31. Additionally, the hollow body preferably has an annular flange 39, or a similarly outwardly protruding structure, which enables manual gripping of the body between two fingers 41 and 42 while the thumb 43 of the user engages second end 33 of the plunger. Additionally, flange 39 extends radially to a sufficient distance to prevent inadvertent insertion of the collection apparatus too far into the vagina of the user.

Mounted proximate open end 28 of body 27 is a specimen contacting means, generally designated 44, which has a central cylindrical portion 46 dimensioned to pass through open front end 28. Plunger 31 cooperates with contacting means 44 so that reciprocation of the plunger to an advanced position from that shown in FIG. 2 displaces central portion 46 of the specimen contacting means beyond the front end 28 of the body to the phantom line position shown in FIG. 2. Moreover, the plunger is also mounted for movement to the retracted position shown in solid lines in FIG. 2 in which the portion 46 of the contacting means is retracted inside body 27.

As thus far described, the components of the apparatus of the present invention are broadly known in the prior art. Thus, hollow bodies with reciprocally mounted plungers and specimen contacting members had been proposed as assemblies for self-testing devices to determine the condition of fluids in body cavities, and particularly in the vagina.

In the improved apparatus of the present invention, however, specimen collecting means 44 is formed of a material suitable for collecting a sufficient quantity of bodily fluids from a cavity to enable transfer of a specimen of the fluids to a separate specimen testing assembly after the collecting means is removed from the body cavity. Moreover, the apparatus of the present invention further includes biasing means resiliently biasing plunger 31 to the retracted position to automatically shield the specimen contacting means from contamination from bodily fluids upon release of manually engageable end 33 of the plunger during insertion and removal of the apparatus from the body cavity.

In the form of the invention shown in FIG. 2, specimen contacting means 44 is formed of a material which absorbs bodily fluids to effect collection and retention of the same. More particularly, specimen collecting means 44 is preferably formed as a resilient sponge, such as, an open cell, polyurethane foam.

Instead of mounting a treated pH paper or other treated material to apparatus 22 for direct contact with fluid specimens in the body cavity, the apparatus of the present invention preferably includes specimen contacting means in the form of a material capable of absorbing the bodily fluids to be tested. Cotton, sponge, paper and other fibers which will absorb or trap sufficient fluids to enable the transfer of a representative specimen are suitable for use with the apparatus of the present invention.

The use of a resilient sponge, however, is particularly advantageous in that the specimen absorbing member 44 has the double function of also providing an automatic retraction or biasing means. Thus, member 44 is preferably formed with an annular slot 45 which defines central cylindrical portion 46 and coaxial surrounding annular peripheral portion 50. Slot 45 does not extend through the full depth of member 44 so that the central and peripheral portions are joined by a common base 55.

Upon displacement of plunger 31 from the solid line retracted position to the phantom line advanced position, first end 32 of the plunger presses into base 55 and displaces cylindrical portion 46 outwardly of end 28 of the collector body. Additionally, base 55 compresses peripheral annular sponge portion 50 between the plunger and interior surface or annular shoulder 60 on the collector body proximate opening 28. The compressed periphery 50 then acts as a spring to urge the central portion 46 back into the collector body 26 when plunger end 33 is released.

The apparatus of FIG. 2 is particularly well suited for self-testing because of the combination of absorption means 44 and spring biasing of the absorption means to the retracted position. If the user simply does not press end 33 of plunger 31, specimen contacting portion 46 of absorption means 44 will be automatically retracted inside body 27. During insertion of the apparatus into the body cavity, therefore, the user can simply use the enlarged end 39 to manipulate the body during insertion until the desired depth has been reached. At that point, the plunger end 33 can be engaged and pressed forward to the phantom line position to cause contact of plunger portion 46 with bodily fluids. After pressing the plunger in, the end 33 can then be released, and absorption portion 46 will automatically retract inside body 27. The user can then withdraw or remove the specimen collecting apparatus 22 by pulling outwardly on flange 39. During both the insertion and removal process, therefore, the collection portion 46 of the apparatus is shielded inside the hollow body from contact with fluids in the vaginal canal prior to reaching the desired test depth. The length of body 27 is selected to position open end 28 for most users in the area of at about one-half the distance between the entry to the vaginal canal and the cervix, taking into account the thickness of the users fingers on flange 39.

If a surplus of body fluids is present in the body cavity, absorption means 44, such as a sponge or cotton, will not be overwhelmed by such excess. The absorption means will simply saturate, but it will not lose its mechanical integrity, nor will any chemicals be present in absorption means 44 which could be overwhelmed by the excess fluids.

Once removed from the body cavity, the user can again press plunger end 33 to extend portion 46 outside open end 28 of the collecting apparatus body. The extended end 46 can then be contacted with specimen testing means 23. More particularly, a treated chemical section or strip 51 can be mounted to card 24, and portion 46 wiped gently across strip 51 to contact strip 51 with a relatively controlled amount of the specimen. Mounted proximate to test strip 51 is comparison means or a color chart 52 for comparison to strip 51. Comparison means 52 includes a plurality of colored areas 53, 54 and 55 representing possible colors which strip 51 may turn or remain as a result of contact with the specimen. Color chart 52 is inert to the body fluids being tested, and is preferably mounted closely proximate strip 51 so that an accurate comparison of the color resulting on strip 51 with predetermined known colors in the chart 52 can be made.

In the preferred form, the apparatus of the present invention is used as a vaginal testing apparatus, and strip 51 is a strip of pH paper. The colors 53, 54 and 55 correspond to various pH levels which allow the user to make a comparison that would enable the user to know whether or not the pH level of her bodily fluids are normal or above or below the levels which would be regarded as healthy and safe.

Figure 3:
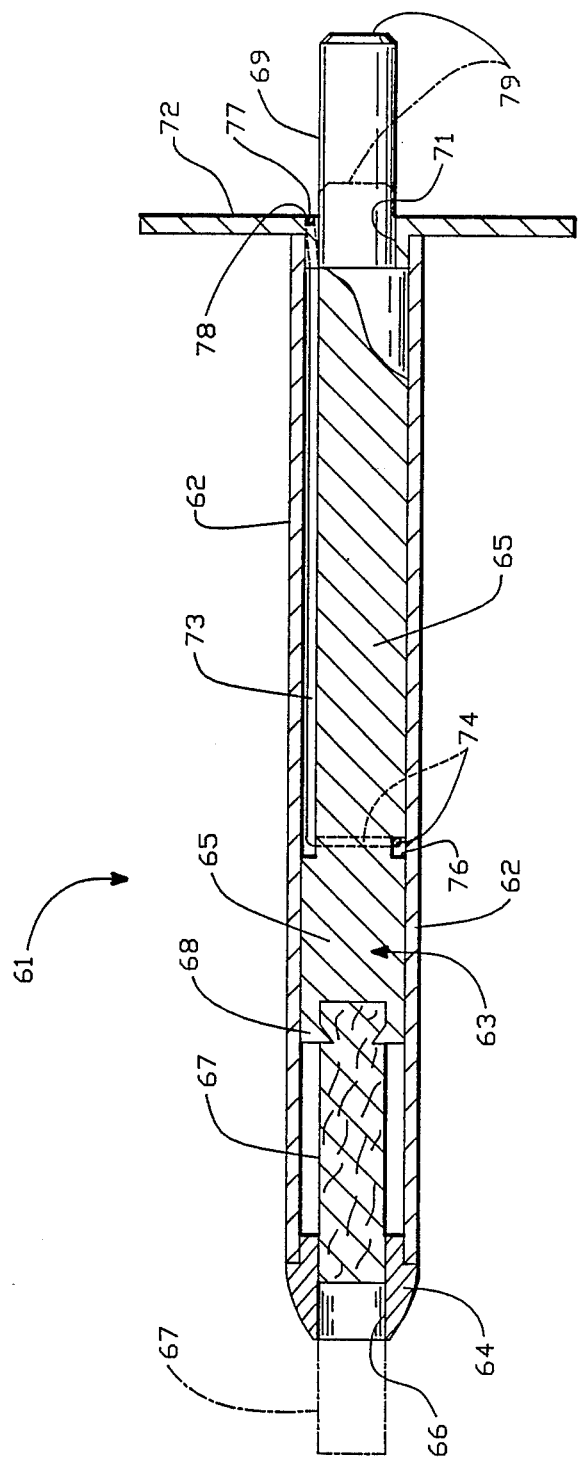
FIG. 3 is a side elevation view corresponding to FIG. 2 of a modified form of the specimen collecting apparatus of the present invention.
Figure 4:
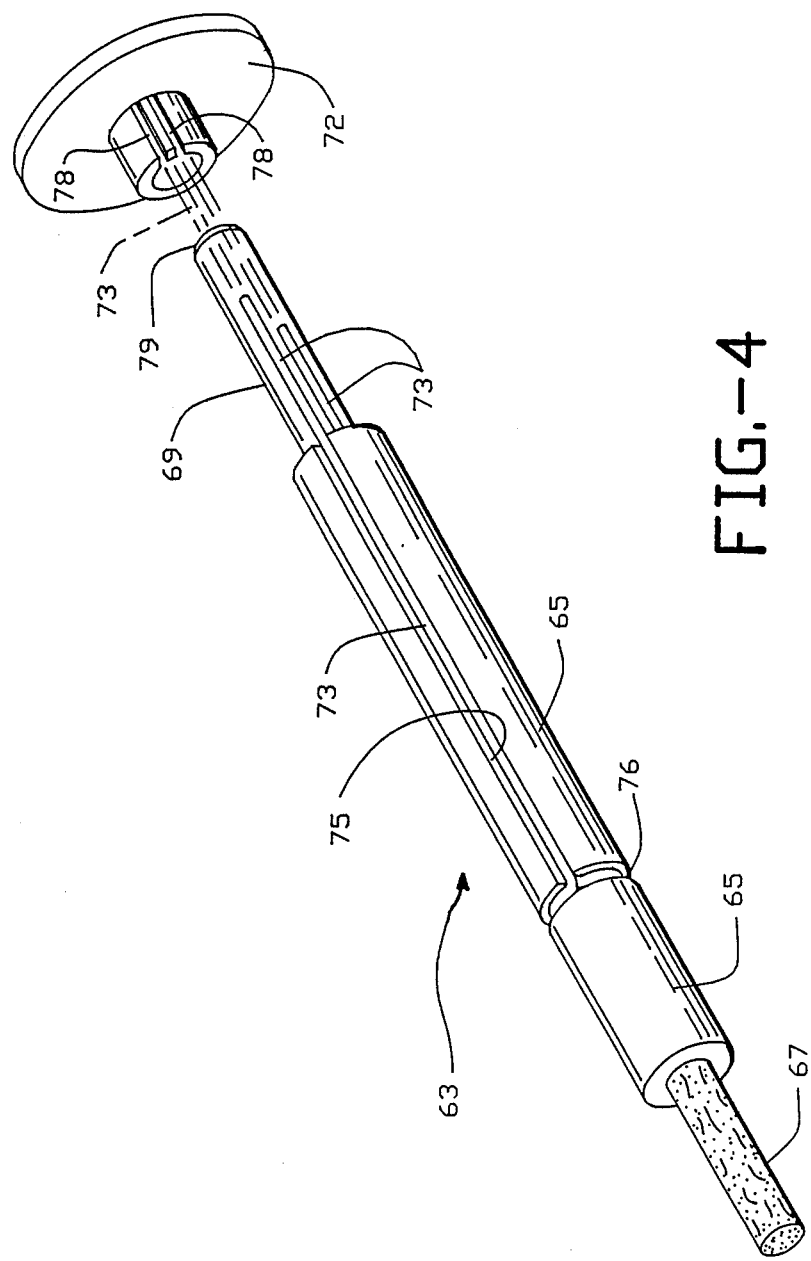
FIG. 4 is a perspective view of the plunger assembly from the specimen collecting apparatus of FIG. 3.

An alternate form of the specimen collecting apparatus of the present invention is shown in FIGS. 3 and 4. Specimen collector 61 can be seen to have a hollow tubular body 62 inside of which plunger assembly, generally designated 63, is reciprocally mounted. Tubular member 62 has a nose or tip 64 formed with a bore or open end 66 through which specimen collecting or absorbing member 67 can be extended. Plunger assembly 63 has a first end 68 which carries the specimen absorbing material 67 and a second end 69 which extends out through a bore 71 in end cap 72. Cap 72 and nose 64 can be adhesively secured in tubular body 62.

In order to resiliently bias the absorption member 67 to the retracted position shown in solid lines in FIG. 3, collector apparatus 61 further includes an endless elastic band member 73 having a portion 74 looped around plunger 63 in a groove 76 formed in the plunger. An opposite portion 77 of band 73 extends around a slot or groove 78 in end cap 72. The body 65 of plunger assembly 63 is formed with a longitudinally extending groove 75 which extends from groove 76 rearwardly along body 65 to the end 69 in order that the rubber band 73 can pass from groove 76 to end cap 72.

Assembly of the rubber band around the plunger and end cap is accomplished by looping a portion of the band in groove 76, running both sides of the band down groove 75, and inserting the band into bore 71 of the end cap and laterally outwardly in the slots or grooves 78 so as to hook the portion 77 of the rubber band to the end cap. Thereafter end 69 of the plunger is inserted into end cap bore 71. With the plunger assembly and end cap held together by band 73, the entire assembly can then be placed into hollow body 62. Thus, band 73 tends to pull the plunger toward end cap 72 to thereby retract absorption member 67. As shown in FIG. 3, absorption member 67 is a cotton or fibrous member dimensioned to pass through or to be in sliding engagement with bore 66 of nose 64.

The specimen collecting apparatus of FIGS. 3 and 4 is used in a manner analogous to the apparatus of FIGS. 1 and 2. More particularly, the user grasps the collecting apparatus body 62 proximate end cap 72, without depressing end 79 of plunger assembly 63. The collector body is then inserted to the desired depth in the canal leading to the body cavity. Once at the desired depth, end 79 of the plunger is depressed to the phantom line position in FIG. 3, which displaces absorption or contact member 67 to the phantom line position shown in FIG. 3. This produces contact of the absorption media with the bodily fluids in the cavity, and the plunger can then be released. The apparatus is then withdrawn with the collected specimen. Thereafter, plunger end 79 is again engaged and advanced to project the absorption media 67 beyond noses 64, and with the media exposed, it is wiped across a test strip, such as strip 51 in FIG. 1. The resulting reaction of the test strip to the bodily fluids can then be compared to color chart 52 in order to enable a diagnosis to be made.

Figure 5:
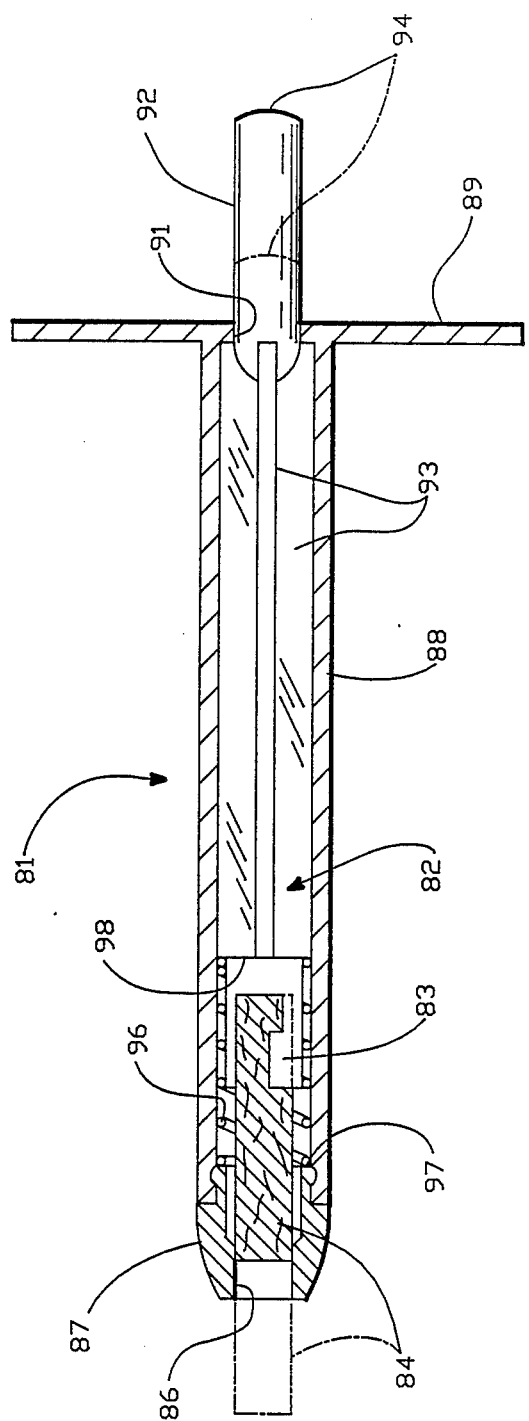
FIG. 5 is a side elevation view corresponding to FIG. 2 of a further modified form of the specimen collecting apparatus of the present invention.

Another form of specimen collecting apparatus is shown in FIG. 5. The collecting assembly, generally designated 81, includes a plunger assembly, generally designated 82, with a first or front end 83 having specimen absorbing member 84 mounted thereto. Absorbing member 84 is dimensioned to pass through bore 86 in nose member 87 which is mounted on the front end of hollow collecting member body 88. The opposite end of body 88 is provided with manually engageable flanges 89 and a bore 91 out of which extends an end 92 of plunger 82. The body 93 of plunger 82 is cruciform in shape. When the end 94 is depressed, the plunger moves to the phantom line position, and a compressive coil spring 96 bearing upon a shoulder 97 on nose member 87 and a second shoulder 98 on plunger body 82 urges the plunger back to the solid line position of FIG. 5. The spring 96 can be seen to be concentrically mounted with respect to the absorption member 84 and end 83 of the plunger.

Use of the collecting apparatus 81 of FIG. 5 is identical to that described in connection with the apparatus of FIGS. 1 and 2 and FIGS. 3 and 4. It also will be understood that it is intended for such collecting apparatus 81 to be used in association with a testing apparatus such as the test strip 51 and color chart 52.

It is intended that the various collecting apparatus 22, 61 and 81 be formed of relatively inexpensive materials such as plastics (injection molded polystyrene) or even paper so that they can be made disposable. It is contemplated that each of the kits be used only once and then thrown away. Thus, a single test strip 51 is provided and the entire kit is preferably enclosed in an envelope after sterilizing the specimen collecting apparatus. The inherent simple construction of the collecting apparatus allows the entire kit to be priced at a level which will permit the user to conduct the self-testing procedure and thereafter dispose of the entire kit.

In the form of the collecting apparatus of FIG. 2, sponge material 44 is adhesively secured proximate the open end 28 of body 27, and it is preferably formed as an open cell polyurethane foam having a density in the range of about 2 to about 3.5 pounds per cubic feet. The ILD hardness of the foam can be in the range of about 50 to about 100. This foam will provide sufficient resiliency, both when dry and when wet, to provide the necessary retraction mechanism. Additionally, such a foam will absorb sufficient bodily fluids to enable transfer of the same to test paper 51.

Most preferably outer portion 50 is heat sealed at slot 45 to close the pores and enhance sliding of center cylinder 46 with respect to portion 50. Sponge means 44 also can be formed of two independent sponge portions which are mounted together to a common base to enable the center to have maximum absorption and the periphery maximum resiliency and minimum sliding friction.

In the form of the invention shown in FIGS. 3-5, the absorption media is preferably a compressed cellulose acetate cylinder which can be adhesively or mechanically secured to the plunger. Cellulose acetate of the type used for biomedical filter applications is usable in the collecting apparatus of FIGS. 3-5. American Filtrona of Richmond, VA, for example, produces cellulose acetate filters under the trademark TRANSORB, and particularly filter material R-2261, which is suitable for use as the absorptive media of the present invention.

In the preferred form, the kit of the present invention is used to determine the pH of vaginal fluids. Accordingly, strip 51 is a strip of pH paper, and color chart 52 may be a chart in which there are three color areas, namely, area 53 which is red, area 54 which is pink and area 55 which is blue, a color indicating that the pH is over 4.5. Alternatively, a two area color chart can be used with one color (e.g., yellow) indicating healthy pH levels and the other color (e.g., brown) indicating unhealthy levels. The color selection obviously depends upon the pH paper employed as strip 51.

What is claimed is:

1. In a body cavity specimen collecting apparatus including an elongated hollow body dimensioned for insertion into a body cavity and having an open front end and an open opposite end, plunger means mounted for reciprocation in said body with a first end proximate said open front end and a manually engageable second end extending outwardly of said opposite end, and specimen contacting means mounted proximate said open end and having a portion of said specimen contacting means dimensioned to pass through said open front end, said plunger means being mounted for reciprocation between an advanced position displacing said portion of said specimen contacting means beyond said open front end and a retracted position with said specimen contacting means retracted inside said body inwardly of said open front end, wherein the improvement in said collecting apparatus comprises:

said specimen contacting means being formed of a sponge material which is resilient prior to contact with said bodily fluids and which is suitable for collecting and retaining a sufficient quantity of bodily fluids from said body cavity to enable transfer of a specimen of said bodily fluids to a separate specimen testing means after said collecting apparatus is removed from said body cavity and said contacting means is brought into contact with said bodily fluids, said sponge material resiliently biasing said plunger means to said retracted position to automatically shield said specimen contacting means from contamination by bodily fluids upon release of said manually engageable end during insertion and removal of said collecting apparatus to and from said body cavity.

2. The specimen collecting apparatus as defined in claim 1 wherein,
said specimen contacting means is a material which absorbs said bodily fluids to effect collection and retention of the same.

3. The specimen collecting apparatus as defined in claim 1 wherein,
said sponge is formed with a central portion dimensioned for passage through said open front end for sampling of said bodily fluids and a peripheral portion mounted for compressive loading between an interior surface of said body proximate said open front end and said plunger means when said plunger means is reciprocated to said advanced position.

4. The specimen collecting apparatus as defined in claim 3 wherein,
said central portion is a cylindrical portion, said peripheral portion is an annular portion coaxial with and surrounding said central portion, and said sponge further includes a common base portion connecting said central portion and said peripheral portion.

5. A specimen collecting apparatus as defined in claim 1, and
specimen testing means forming a collection and testing kit with said specimen collecting apparatus, said collecting apparatus being manipulatable independently of said specimen testing apparatus and said kit, and said specimen testing means having a test section treated with a compound which is reactive to contact with bodily fluids.

6. A specimen collecting apparatus as defined in claim 5 wherein,
said specimen testing means further includes comparison means having visually perceptible indicia mounted immediately proximate said test section for visual comparison of the effect of said bodily fluids on said test section to said comparison means.

* * * * *